US008610076B2

(12) United States Patent
Blevis

(10) Patent No.: US 8,610,076 B2
(45) Date of Patent: Dec. 17, 2013

(54) SYSTEM AND METHOD FOR MOLECULAR BREAST IMAGING

(75) Inventor: Ira Blevis, Zichron Yaakov (IL)

(73) Assignee: General Electric Company, Schenectady, NY (US)

( * ) Notice: Subject to any disclaimer, the term of this patent is extended or adjusted under 35 U.S.C. 154(b) by 57 days.

(21) Appl. No.: 13/304,257

(22) Filed: Nov. 23, 2011

(65) Prior Publication Data

US 2012/0148016 A1    Jun. 14, 2012

Related U.S. Application Data

(60) Provisional application No. 61/417,350, filed on Nov. 26, 2010.

(51) Int. Cl.
*G01T 1/20* (2006.01)

(52) U.S. Cl.
USPC .................................... 250/363.01

(58) Field of Classification Search
USPC ........ 250/363.01–363.1, 362, 370.01–370.15
See application file for complete search history.

(56) References Cited

U.S. PATENT DOCUMENTS

| 6,778,632 | B2 | 8/2004 | Hoheisel et al. |
|---|---|---|---|
| 7,742,561 | B2 | 6/2010 | Ueki |
| 2010/0104505 | A1 | 4/2010 | O'Connor |
| 2010/0187425 | A1 | 7/2010 | Majewski et al. |
| 2010/0260316 | A1 | 10/2010 | Stein et al. |
| 2010/0261997 | A1 | 10/2010 | Ren et al. |
| 2010/0329418 | A1 | 12/2010 | Blevis |
| 2010/0329419 | A1 | 12/2010 | Blevis |

OTHER PUBLICATIONS

Hruska et al., "Molecular breast imaging—A phantom sutdy on the impact of collimator selection on detection of sub-10 mm breast lesions," 2006, Nuclear Instruments and Methods in Physics Research A, vol. 569, pp. 250-254.*
Robert et al., "Simulation-based optimization of a parallel collimator for scintimammography using anew CdZnTe camera—camera architecture (HiSens),"2009, IEEE Nuclear Science Symposium Conference Record, pp. 2641-2645.*
Wieczorek et al., "Collimator spatial resolution," 2005, IEEE Nuclear Science Symposium Conference Record, pp. 1717-1721.*
Blevis et al, "CZT gamma camera with pinhole collimator: spectral measurements," 2008, IEEE Nuclear Scince Symposium Conference Record, pp. 4931-4932.*
M. Wernick and J. Aarsvold, Emission Tomography: The Fundamentals of PET and SPECT, Elsevier Academic Press, Copyright 2004, Elsevier, Inc., pp. 161-164.
O'Connor, M. K. et al. "Molecular Breast Imaging Using a Dedicated High-Performance Instrument" Proc. of SPIE vol. 6319, 63191D (2006).
Smith, M. F. et al. "Optimizing Pinhole and Parallel Hole Collimation for Scintimammography with Compact Pixellated Detectors" Nuclear Science Symposium, 2002 IEEE, pp. 1806-1809 vol. 3, Nov. 10-16, 2002.

* cited by examiner

*Primary Examiner* — Kiho Kim
(74) *Attorney, Agent, or Firm* — The Small Patent Law Group; Dean D. Small

(57) ABSTRACT

A system and method for a molecular breast imaging (MBI) are provided. One MBI system includes at least one cadmium zinc telluride (CZT) detector having a plurality of pixels and a registered parallel hole collimator coupled to a face of the CZT detector. The registered parallel hole collimator includes a plurality of collimator holes, wherein the plurality of collimator holes are aligned with the plurality of pixels, and the spatial dimensions of the plurality of holes are configured based on characteristics of the CZT detector and the registered parallel hole collimator.

22 Claims, 6 Drawing Sheets

SYSTEM AND METHOD FOR MOLECULAR BREAST IMAGING

CROSS REFERENCE TO RELATED APPLICATIONS

This application claims priority to and the benefit of the filing date of U.S. Provisional Application No. 61/417,350, filed Nov. 26, 2010, which is hereby incorporated by reference in its entirety. This application relates to U.S. application Ser. No. 13/036,831, filed Feb. 28, 2011, which claims priority to U.S. Provisional Application No. 61/311,189, filed Mar. 5, 2010, and also relates to U.S. application Ser. No. 12/493,382, filed Jun. 29, 2009, the subject matter of all of which is hereby incorporated by reference in their entirety.

BACKGROUND OF THE INVENTION

The subject matter disclosed herein relates generally to systems and methods for diagnostic medical imaging, and more particularly to Molecular Breast Imaging (MBI) systems.

Molecular Breast Imaging (MBI) is used to image breasts to detect cancer. MBI can be used to image breasts having radiographically dense breast tissue. The typical radiation dose administered using MBI systems is not as low as x-ray mammography (XRM). Accordingly, the use of MBI has some limitations, for example, to the high risk population subset, or to those for which XRM is inconclusive. Accordingly, it would be desirable to reduce the procedure time, increase the diagnostic confidence, and/or reduce the dose when using MBI systems.

BRIEF DESCRIPTION OF THE INVENTION

In accordance with various embodiments, a molecular breast imaging (MBI) system is provided that includes at least one cadmium zinc telluride (CZT) detector having a plurality of pixels and a registered parallel hole collimator coupled to a face of the CZT detector. The registered parallel hole collimator includes a plurality of collimator holes, wherein the plurality of collimator holes are aligned with the plurality of pixels, and the spatial dimensions of the plurality of holes are configured based on characteristics of the CZT detector and the registered parallel hole collimator.

In accordance with other various embodiments, an MBI system is provided that includes at least one cadmium zinc telluride (CZT) detector having a plurality of pixels and a registered parallel hole collimator coupled to a face of the CZT detector. The registered parallel hole collimator includes a plurality of collimator holes, wherein the plurality of collimator holes are aligned with the plurality of pixels. A height of the registered collimator is about 2 centimeters and a pitch is about 2.5 millimeters, with a 9:1 aspect ratio.

In accordance with still other various embodiments, an MBI system is provided that includes a pair of cadmium zinc telluride (CZT) detectors each having a plurality of pixels and configured to immobilize an object therebetween. The MBI system further includes a registered parallel hole collimator coupled to a face of each of the CZT detectors and having a plurality of collimator holes. The plurality of collimator holes are aligned with the plurality of pixels, and the spatial dimensions of the plurality of holes are configured based on characteristics of the CZT detectors and registered parallel hole collimators.

DETAILED DESCRIPTION OF THE INVENTION

Figure 1:
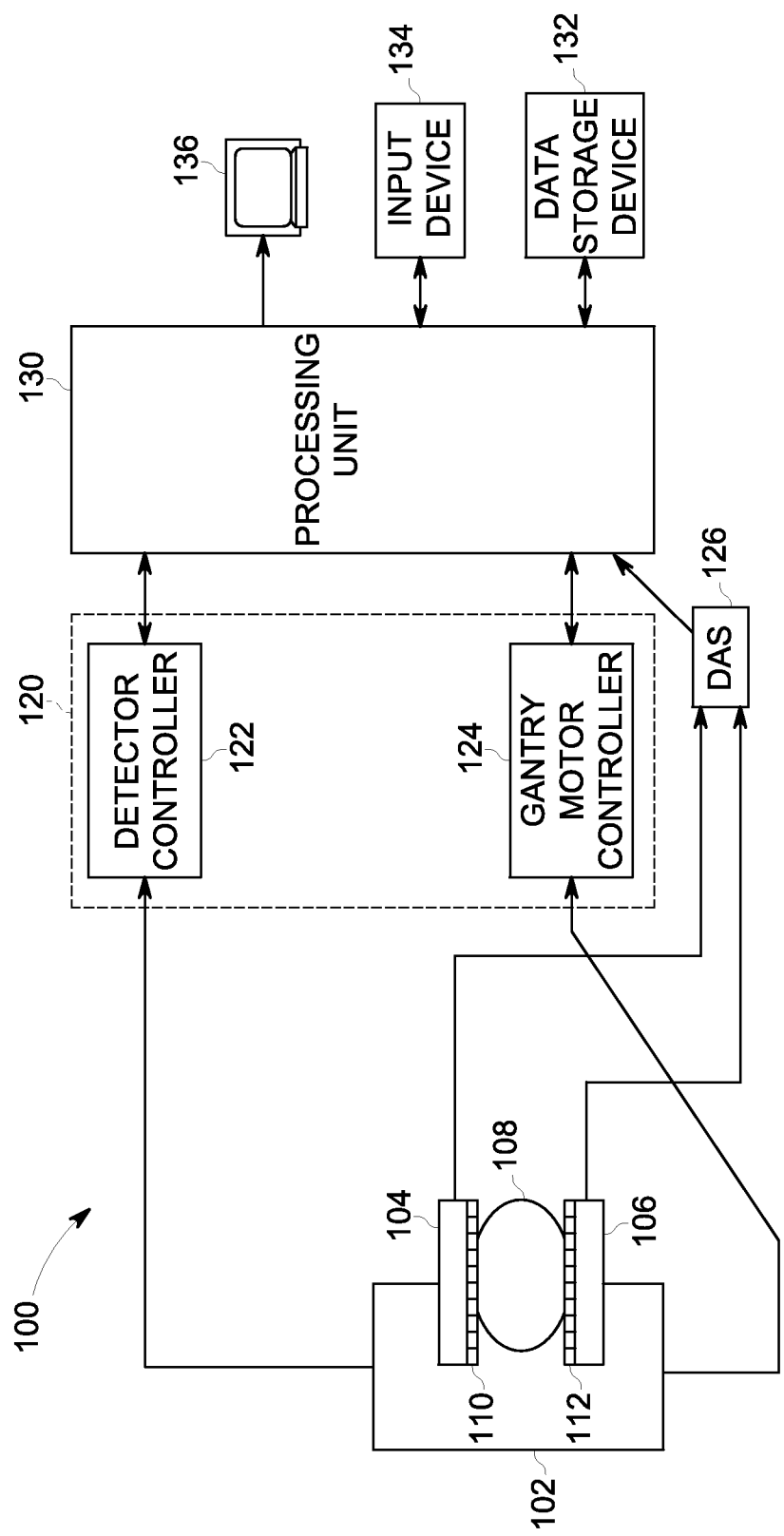
FIG. 1 a block diagram of an exemplary nuclear medicine imaging system embodied as a Molecular Breast Imaging (MBI) system constructed in accordance with various embodiments and in connection with which various embodiments of a collimator may be implemented.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide a collimator arrangement for a Nuclear Medicine (NM) imaging system that may include one or more detectors. For example, various embodiments provide a collimator arrangement for a dual-headed (also referred to as a dual-head) Molecular Breast Imaging (MBI) system, such as an MBI system having a pair of detectors. The dual-head configuration generally provides increased sensitivity (versus single detector systems) and two independent (but still co-linear) views. By practicing at least some of the various embodiments, reduced procedure time, increased diagnostic confidence, and/or reduced dose using MBI may be provided. In accordance with various embodiments, the sensitivity of a dual-headed system is increased, as well as decreasing scanning time, increasing confidence or decreasing dose, for example, by a factor or more (such as a factor of 4). Accordingly, sensitivity (as well as time, confidence and dose) may be increased by practicing the various embodiments.

More particularly, in various embodiments a collimator arrangement and/or configuration are provided for an MBI system having one or more detectors. It should be noted that although a dual-headed detector configuration is described, various embodiments may be implemented in connection with a single headed detector system. As illustrated, the collimator arrangement is matched to a dual-head configuration MBI system. For example, a collimator system formed in accordance with various embodiments may be provided in an MBI system 100 as illustrated in FIG. 1. The system 100 includes imaging detectors 104 and 106 mounted on or to a gantry 102. Each detector 104 and 106 generally captures a two-dimensional image that may be defined by the x and y location of the pixel and the detector number. Further, in other exemplary embodiments, at least one of the detectors 104 and 106 may change orientation relative to a stationary or movable gantry 102. The detectors 104 and 106 may be registered such that features appearing at a given location in one detector can be correctly located and the data correlated in the other detector. Accordingly, in various embodiments common features in the two images acquired by the imaging detectors 104 and 106 can be combined.

Each of the detectors 104 and 106 has a radiation detection face (not shown) that is directed towards a structure of interest, such as an object, for example, a breast 108 therebetween that may have a lesion. Collimators 110 and 112 are provided in combination or connection with the detectors 104 and 106, respectively. In various embodiments, the radiation detection faces of the detectors 104 and 106 are covered by the collimators 110 and 112. In some embodiments, the collimators 110 and 112 are registered parallel holes collimators coupled to the detection faces of the detectors 104 and 106.

For example, the detectors 104 and 106 may include collimators 110 and 112, respectively, provided directly on the surface of the detectors 104 and 106 and illustrated as parallel hole collimators. The detectors 104 and 106 are also capable of being rotated to some angle to provide various images of the breast 108 while remaining substantially parallel to each other. Additionally, the distance between the two detectors may be changed to accommodate breasts with different sizes and to immobilize the breast for the duration of data acquisition, which may include applying light pressure to the breast. The distance between near faces of the two collimators 110 and 112 is registered automatically or manually. Although illustrated as a parallel hole collimators 110 and 112, different types of collimators as known in the art may be used, such as pinhole, fan-beam, cone-beam, and diverging type collimators. An actual field of view (FOV) of each of the detectors 110 and 112 may be directly proportional to the size and shape of the respective imaging detector, or may be changed using collimation.

A motion controller unit 120 may control the movement and positioning of the gantry 110 and/or the detectors 104 and 106 with respect to each other to position the breast 108 within the FOVs of the imaging detectors 104 and 106 prior to acquiring an image of the breast 108. The controller unit 120 includes a detector controller 122 and a gantry motor controller 124 that may be automatically commanded by a processing unit 130, manually controlled by an operator, or a combination thereof. The gantry motor controller 124 and the detector controller 122 may move the detectors 104 and 106 with respect to the breast 108 individually, in segments or simultaneously in a fixed relationship to one another. Alternatively, one or more collimators may be moved relative to the detectors 104 and 106. The distance between the detectors 104 and 106 may be registered by the controller 120 and used by the processing unit 130 during data processing. In some embodiments, motion is manually achieved and the controller 120 is replaced with scales or encoders for measuring the distance between the detectors 104 and 106, the detector orientation, and/or any immobilization force exerted by at least one detector 104 and/or 106 on the breast 108.

During operation, the breast 108 is positioned between the detectors 104 and 106 and at least one detector is translated to immobilize the breast 108 between the detectors 104 and 106. The detectors 104 and 106 are then used to acquire image data of the breast 108, which may include one or more lesions, for example a breast cancer tumor, within the breast 108. The detectors 104 and 106 and gantry 110 generally remain stationary after being initially positioned, and imaging data is acquired. The imaging data may be combined and reconstructed into a composite image comprising two-dimensional (2D) images.

A Data Acquisition System (DAS) 126 receives analog and/or digital electrical signal data produced by the detectors 104 and 106 and decodes the data for subsequent processing in the processing unit 130. A data storage device 132 may be provided to store data from the DAS 126 or reconstructed image data. An input device 134 (e.g., user console with keyboard, rollerball, etc.) also may be provided to receive user inputs and a display 136 may be provided to display reconstructed images.

Figure 2:
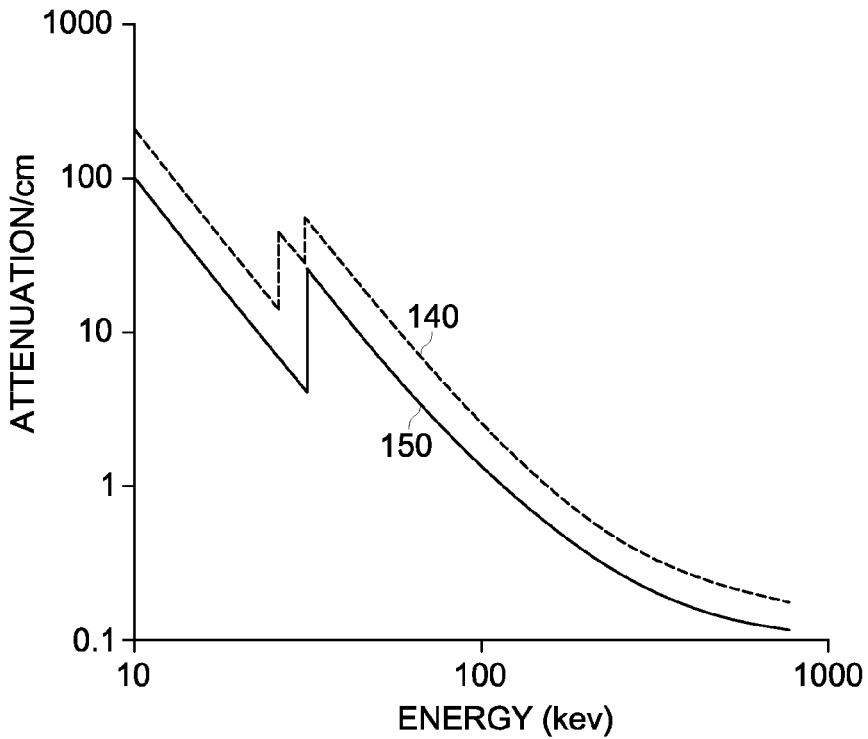
FIG. 2 is a graph illustrating a stopping power comparison.

In various embodiments, the detectors 104 and 106 may be formed of cadmium zinc telluride (CZT) tiles or alternatively any two-dimensional pixelated detector. CZT is a direct conversion semiconductor with a density of about 5.8 g/cm$^3$. The density of CZT and high effective atomic number ($Z_{eff}$~50) give CZT high stopping power for typical energies of interest, such as in Single Photon Emission Computed Tomography (SPECT). Additionally, CZT also, for example, has a linear attenuation coefficient greater than that of NaI. A comparison of stopping power is illustrated in FIG. 2. As illustrated by the curves 140 and 150, the linear attenuation coefficient of NaI and CZT show that the linear attenuation coefficient of CZT has greater stopping power at the energy levels.

It should be noted that the zinc content in the CZT can vary, but a typical composition is $Cd_{(1-x)}Zn_xTe$ with x around 0.1. The CZT often contains trace amounts of other elements (dopants) that are used to improve the electrical properties. The CZT may be grown as a single crystal at a temperature of around 1100 C in a hermetically sealed container to prevent chemical contamination. The crystal (known as "boule") is cut into wafers, polished, and metal contacts are deposited on the surface to extract the electrical signals from the detector, and is bonded to electronics to form a detector.

Figure 3:
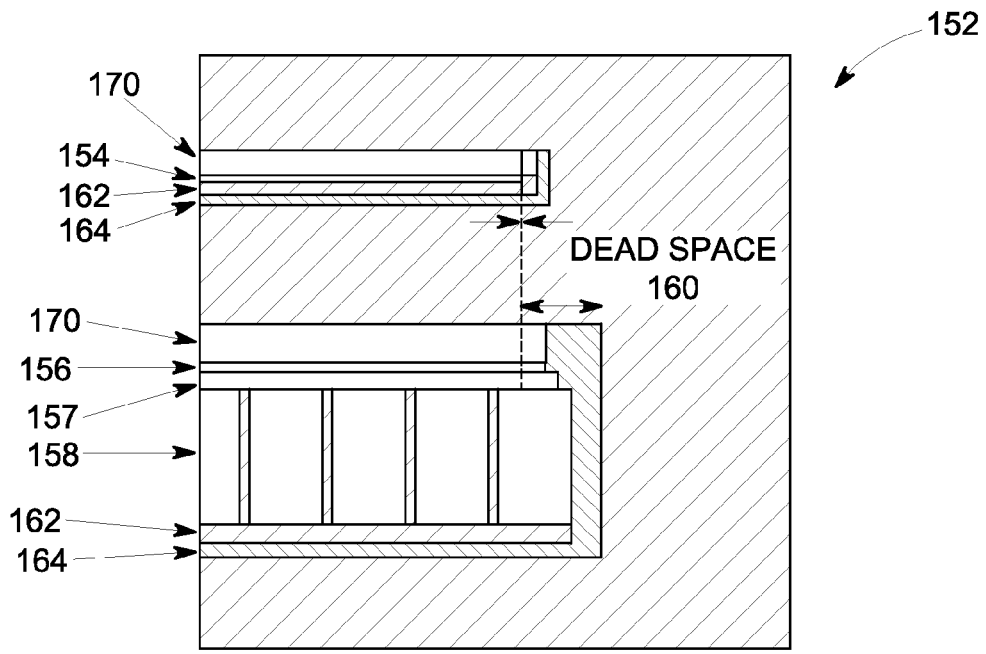
FIG. 3 is a diagram illustrating an Anger camera.

In a typical scintillator-based gamma camera 152 as illustrated in FIG. 3, (which may include collimators 170) incident gamma rays deposit energy in the scintillator 156 where the energy is converted into visible (or near-UV) light photons. The number of photons generated varies with the scintillator 156, but for NaI:Tl (thallium-doped sodium iodide, the "standard" scintillator for Anger cameras) the conversion rate is typically 38 photons/keV; thus, the 140 keV emission from $^{99m}Tc$ produces about 5300 photons. Two-thirds of these photons reach the photocathode of a photomultipliers (PMTs) 158, where about 25% of the photons are converted to photoelectrons (and may be guided using a lightguide 157). These photoelectrons are amplified by the PMT 158 and turned into an electrical pulse by electronics 162 (which may be shielded by shielding 164) with an amplitude proportional to the deposited energy. The amplitude of the electrical signal observed for the same energy deposited is affected by many factors including, for example, variation in the number of photons generated, variation in the number of photons transported to the photocathode (which depends on depth of interaction), variations in the conversion efficiency of the photocathode, variations in the amplification properties of the PMT dynodes, and statistical fluctuations (Poisson noise), among others.

In a direct conversion detector, such as a detector formed from CZT, the radiation deposits energy at some point in the crystal lattice where the energy deposition results in the generation of pairs of charge carriers. By application of an electric field, the charge carriers are swept to the cathode and anode of the device where the charge carriers induce a current pulse that can be detected. The energy resolution for either detector is limited by Poisson statistics: the full width at half maximum (FWHM) energy resolution is then no better than 2.355/sqrt(N), which sets a limit of 7% FWHM on NaI at 140 keV (with about 1000 UV photons detected), but less than 1.5% FWHM for CZT (with over 30,000 electric charges detected).

It should be noted that the resolution obtained with NaI detectors is a little closer to the theoretical value (10% vs 7%) than for CZT (6% vs 1.5%). However, CZT detectors generally have smaller dimensions. Moreover, in an Anger camera 152 as illustrated in FIG. 3, it is difficult to resolve the position of events beyond the center of the last (edge) PMT. This results in a significant dead space 160 all around the detector 154 as illustrated in FIG. 3. The CZT detector, being direct-conversion based, has no such dead space. A CZT-based detector is also much thinner than an Anger camera since the CZT-based detector contains no lightguide 157 or PMT 158. Thus, the volume that needs to be shielded is much smaller for a CZT-based detector, which in turn results in a final assembly that can be much lighter.

The spatial resolution of CZT detectors (which may be embodied as the detector 104 and/or 106 shown in FIG. 1) in accordance with some embodiments is 2.5 mm, independent of energy, which is better than the 4.0 mm typically achieved with NaI at $^{99M}$Tc energies (140 keV), and even better again than the resolution obtained with $^{201}$Tl (5-6 mm). The greater spatial resolution of CZT detectors results because the photons in a NaI crystal are diffused over a considerable distance before being detected, and the triangulation to the origin of the photons is performed with PMTs 158 that are several centimeters away from the location of radiation interaction. By comparison, in CZT, a compact charge cloud is detected by a segmented anode that is only millimeters away. Thus, an improvement in resolution can be obtained by making the anode pixels smaller and increasing the number of electronic channels. Resolution is then determined by the density of the electronics (or limits thereof), and the associated power dissipation and cost, as well as collimator sensitivity. Thus, system sensitivity in various embodiments takes into account both collimator sensitivity and the stopping power of the detector. Some embodiments include CZT detectors having 0.6 mm pixels, which may be used, for example, for certain astrophysical experiments.

The detector of a gamma camera is often considered separate from the collimator, however, one does not function without the other. For example, intrinsic resolution of a detector (the detector 104 and/or 106 shown in FIG. 1) is considered in conjunction with the corresponding resolution in the collimator (the collimator 110 and/or 112 shown in FIG. 1) in order for the parameter to become meaningful. Similarly, the sensitivity of a collimator does not matter unless the stopping power of the detector is taken into account.

Figure 4:
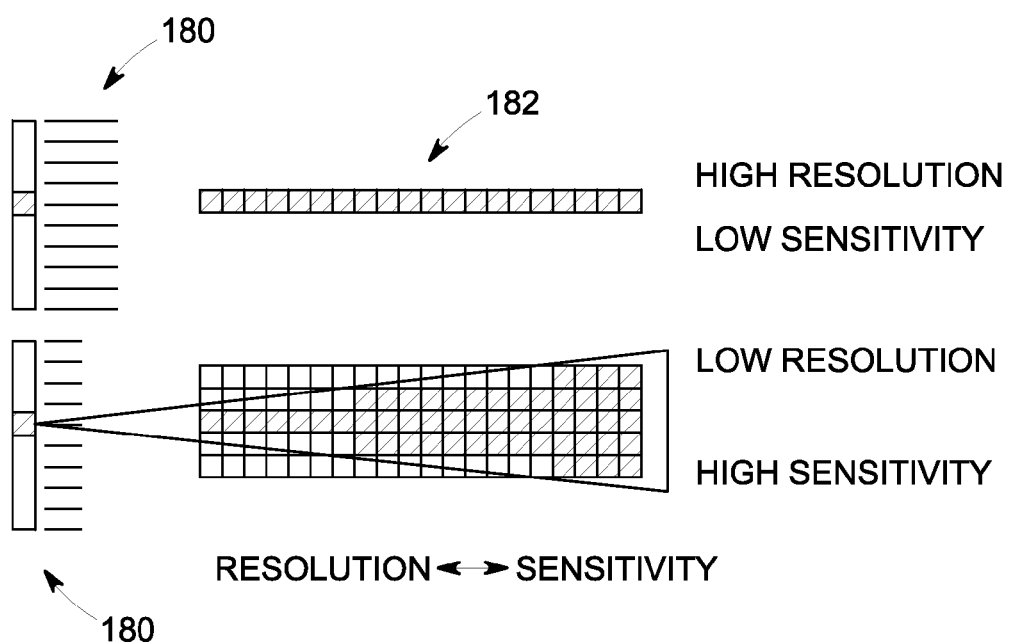
FIG. 4 is a diagram illustrating a tradeoff between detector resolution and sensitivity.

In accordance with various embodiments, a gamma camera acquires image information to create an accurate representation of the activity distribution in a body. It should be noted that there are trade-offs between sensitivity and resolution, namely that a high-resolution collimator 180 views a very narrow column of activity 182 from the patient, and therefore provides excellent spatial resolution at the expense of sensitivity. A high sensitivity collimator, by contrast, accepts radiation from a wider range of angles, which increases the sensitivity at the expense of resolution. These tradeoffs are illustrated n FIG. 4. Other factors and variables also may be used, for example, as described in U.S. Provisional Application No. 61/311,189 filed on Mar. 5, 2010, entitled "System and Method for Molecular Breast Imaging", which is hereby incorporated by reference in its entirety.

It should be noted that a high sensitivity collimator can outperform a high-resolution collimator when the collimator is closer to the patient. The same is the case even when the intrinsic resolution of one system is higher than that of another system. Imaging performance may be based on or comes about as a result of the interaction of all of the factors described above, and imaging performance can be improved or optimized by taking a system approach as discussed in more detail herein in accordance with various embodiments.

It also should be noted that image reconstruction techniques using PSF (point spread function) modeling may be provided to allow the reconstruction of images with higher resolution than is shown by these curves. However, even with these algorithms, for equal count statistics, the image quality obtained with higher resolution collimators will be greater.

Different imaging systems based on CZT technology may be provided in connection with the various embodiments. For example, two exemplary systems that use CZT detectors are the Discovery NM 530c and Discovery NM/CT 570c with Alcyone Technology dedicated cardiac cameras also available from GE Healthcare. Some embodiments of these systems are configured to provide a plurality of detectors 250 as close to the heart as possible in order to be able to image the heart without detector motion. Once again, the CZT detectors in these systems provide excellent increased resolution (which permits the use of pinholes in the minifying configuration) and low dead space, which allows close packing of detectors. The energy resolution of the detectors is also good enough for the potential of simultaneous imaging of $^{123}$I and $^{99m}$Tc labeled agents.

Collimation in accordance with various embodiments may be used with the system described above, as well as other exemplary systems that use CZT are MBI systems, such as those described in more detail herein. For breast imaging, spatial resolution and dead space are two factors for image quality. With the compact form factor and minimal dead space of the CZT detector, a gamma camera formed in accordance with various embodiments is positioned close to the patient, with potential for both CC and MLO views. At the same time, the smaller size of the camera can be less intimidating for the patient. Moreover, and in accordance with various embodiments, with the detector close to the breast, the collimators are configured to be shorter (e.g., less than 35 mm in height), resulting in high sensitivity without sacrificing resolution.

The various embodiments may provide collimators for CZT detectors that are configured to provide imaging for lesions of particular sizes or ranges of sizes. For example, a current standard of care is to detect 5 mm diameter lesions with 10:1 tumor to background concentration. However, it should be noted that other parameters may be used, such as to detect lesions of greater (e.g., 10 mm) diameter or smaller (e.g., less than 5 mm) diameter or different aspect ratios, for example, between 5:1 and 50:1.

For example, a dual-head camera, such as illustrated in FIG. 1, that is formed from two single head cameras (which may be embodied as the detectors 104 and 106 shown in FIG. 1) with registered parallel hole collimators (the collimator 110 and/or 112 shown in FIG. 1) may have a performance that is double that of the single head camera. For example, the two views provide double the data collection rate (the sensitivity of parallel hole collimators for localized sources does not depend on the distance from the source to the collimator as long as the image is not bigger than the field of view). However, in accordance with various embodiments, the dual head camera can have an increase in sensitivity that is greater than two, for example, a sensitivity increase of four times using one or more collimators of the various embodiments described herein.

Various configurations will now be described. Because the maximum distance from lesion to the collimator is halved in a dual head configuration, the collimators of the various embodiments are configured to achieve a target resolution at half the distance compared to a single head design. Moreover, because of the geometrical optics of the parallel hole collimator, the sensitivity corresponding to that resolution is greater, for example four times greater than that of the single head. For example, in some embodiments, in the dual head design, one of the two heads, which ever is closer, can have a four times increase in sensitivity over the single head design for the target tumor. Additionally, the image from the further head also contributes to the detection of the tumor when an algorithm for combining data is used, such that the sensitivity increase will be greater, for example, than four, for example, as high as eight for tumors larger than the target resolution.

Figure 5:
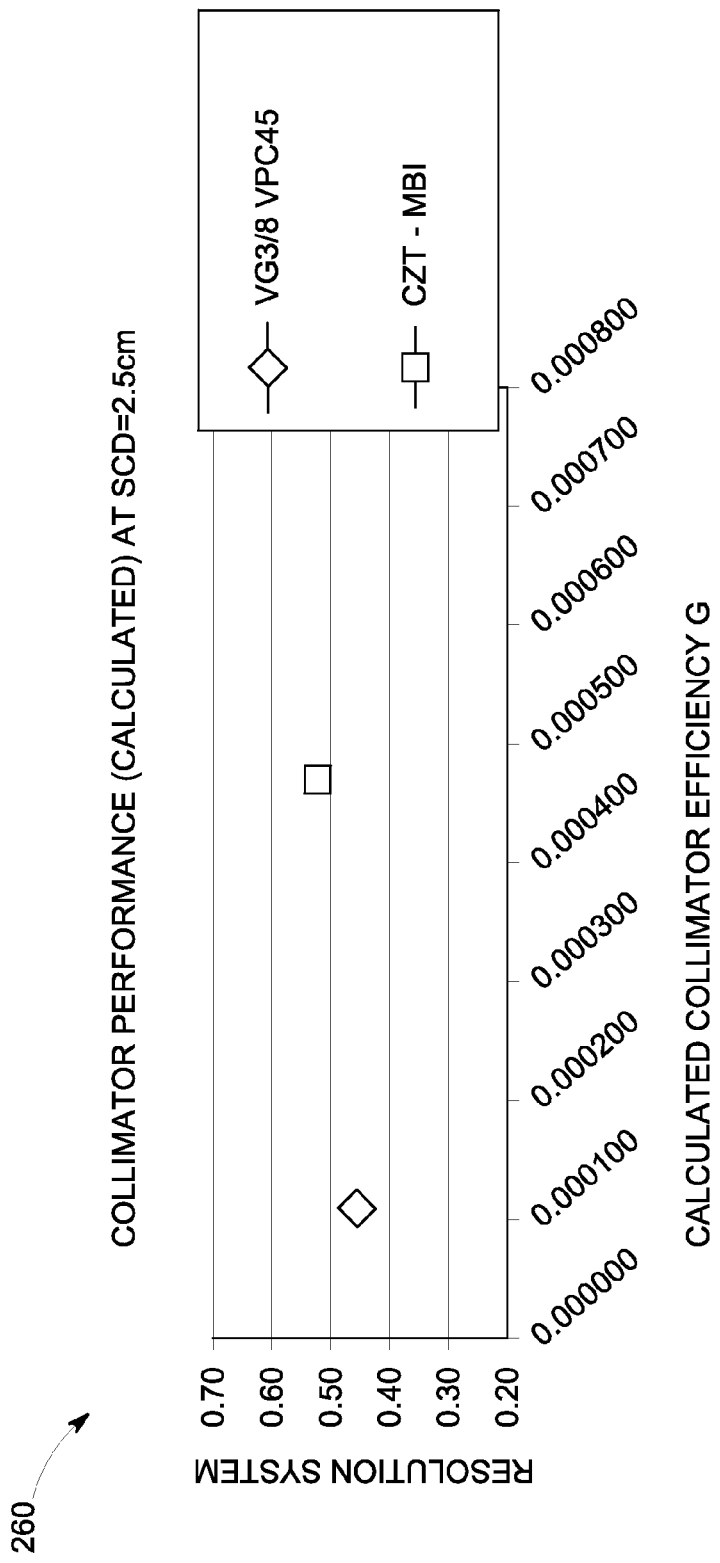
FIG. 5 is a graph illustrating a collimator performance comparison.
Figure 6:
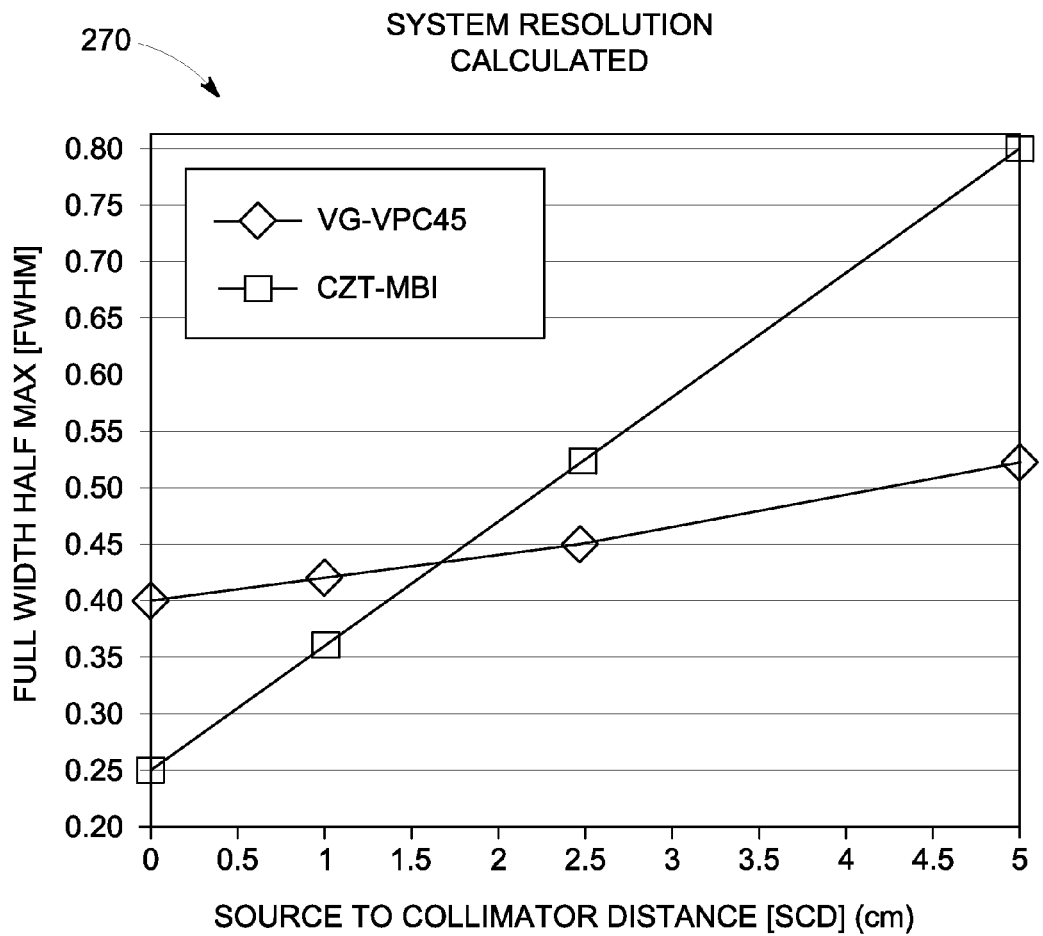
FIG. 6 is a graph illustrating a system resolution comparison.

The graph 260 of FIG. 5 shows collimator performance for a CZT MBI embodiment with a dual head collimator configured (e.g., optimized) for about 0.5 cm (e.g., 0.52 cm) resolution at a distance of 2.5 cm. The graph illustrates that VG-VPC45 (conventional system) has this resolution at 5 cm. The graph 270 of FIG. 6 shows that at 2.5 cm the resolution of the conventional system is a little improved over the CZT dual head (not as improved as discussed above because the intrinsic resolution is worse), but the efficiency is almost ⅕.

In some embodiments, the height of the collimator and the size of the collimator holes are configured such that the resolution of the collimator is provided (or limited) based on the size of the minimum size of a lesion to be detected.

Figure 7:
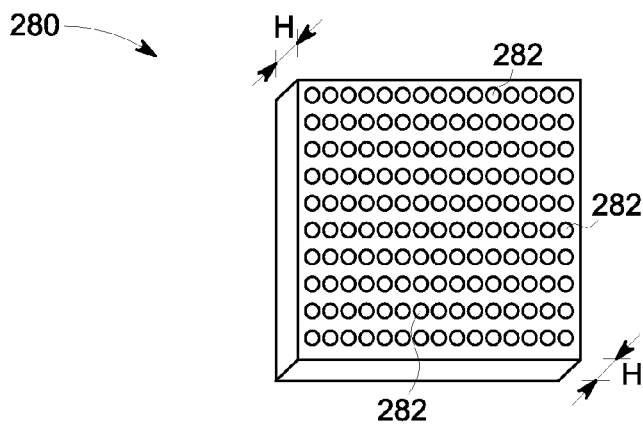
FIG. 7 is a plan view of a collimator arrangement formed in accordance with various embodiments.

Various embodiments provide a shorter collimator height, for example, extending from the surface of the detector. The various embodiments also may have a larger collimator hole size. For example, the larger collimator hole size may be a larger opening for the height of the collimator. For example, in various embodiments, a collimator 280 as shown in FIG. 7 may be provided having a height (H) of the collimator 280 between about 10 mm and about 30 mm and the hole size of the collimator holes 282 is between about 1 mm and 3 mm. However, it should be noted that the height of the collimator 280 and size of the collimator hole opening may be varied as desired or needed. It also should be noted that the height and size of the openings of the holes 282 may be varied in the same or different proportions. In some embodiments, and for example, the collimator height is about 21 mm and the collimator hole size is about 2.1 mm, which results in a 2.5 mm distance from the center of one hole 282 to the center of another hole 282. In such embodiments, the wall thickness of the collimator is about 0.4 mm. It should be noted that as used herein, the term hole refers to any opening of any size and of any shape, and not just round openings. It also should be noted that in various embodiments, there is one hole per pixel of a detector to define a registered collimator. It further should be noted that the collimator 280 may be sized and shaped differently, for example, square, rectangular, etc.

The collimator 170 may be an optimized registered parallel hole collimator. In various embodiments, optimized means that the spatial dimensions of the collimator 280 (e.g., collimator height) and the size (e.g., diameter) of the holes 282 may be determined and formed based on one or more characteristics of the detector or collimator, for example, based on one or more of: (i) the material used to form the collimator 280, which in some embodiments is CZT and (ii) the detector head configuration (e.g., single head or dual head configuration). As used herein, in some embodiments, an optimized collimator means the resolution of the collimator no better or greater than the smallest object at the furthest distance to be imaged by the detector(s). For example, in same embodiments an MBI system may be provided wherein the spatial dimensions of the plurality of collimator holes are configured having a collimator resolution of no greater than 5 millimeters FWHM at a 2.5 centimeter distance from the collimator 280 (e.g., registered parallel hole collimator). As another example of a configuration, the MBI system may be provided wherein the height of the collimator 280 (e.g., registered parallel hole collimator) is about 2 centimeters and a pitch is about 2.5 millimeters, with a 9:1 aspect ratio. In various embodiments a high efficiency collimator, for example, the collimator 280 may be optimized as described herein for operation in a dual-headed detector or camera system, such as a system having a pair of CZT detectors. It should be noted that an MBI system provided with collimation in accordance with various embodiments may be optimized to operate at different distances from a focal view/spot or object to be imaged. For example, the collimator 280 may provide a resolution of 2.5 centimeters at a distance of 3.0 centimeters or 3.5 centimeters (instead of 2.5 centimeters), as well as at other distances.

Figure 8:
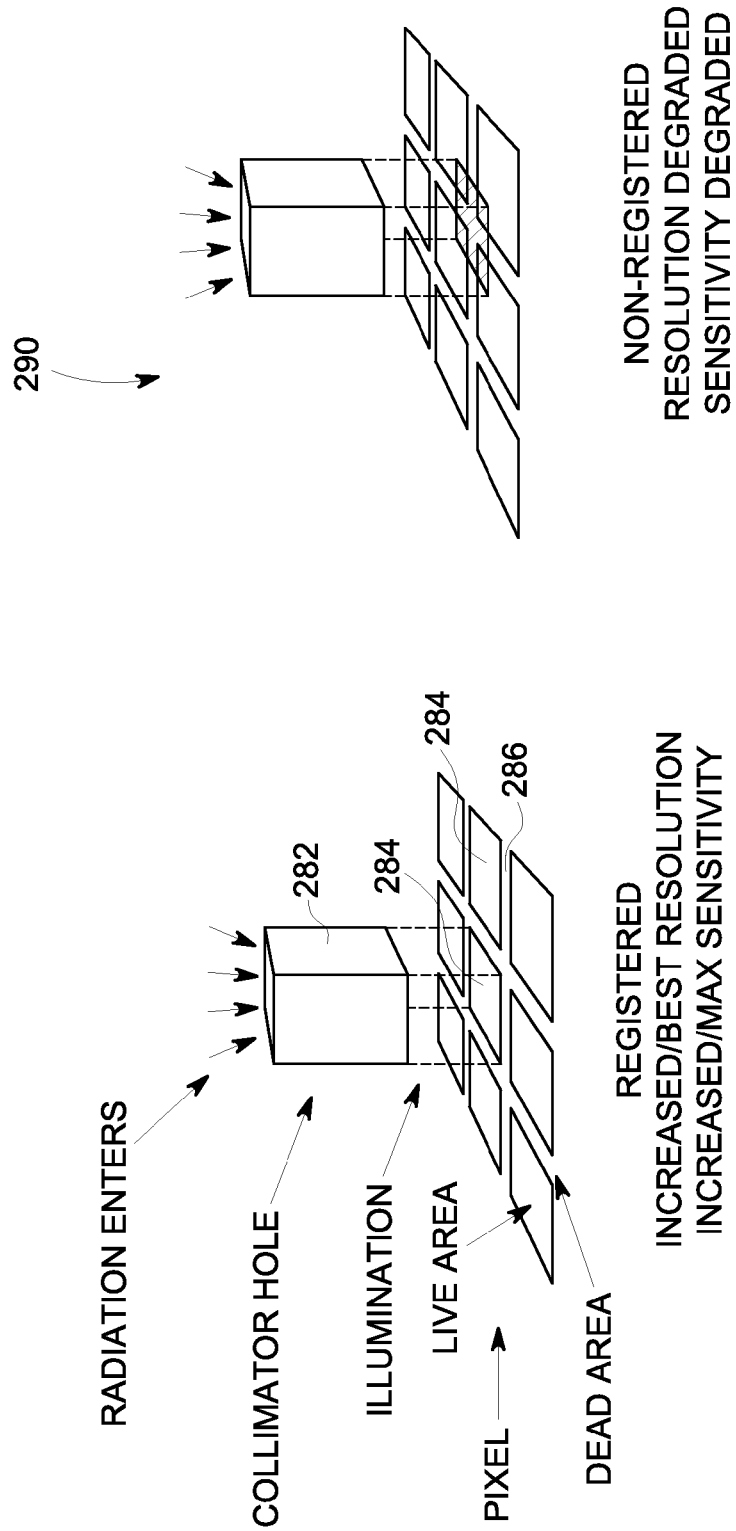
FIG. 8 is a diagram illustrating registered collimation in accordance with various embodiments.

FIG. 8 shows a portion of the collimator 280, namely one of the collimator holes 282, and illustrates a registered collimator configuration. As can be seen, radiation enters the collimator holes 282 (only one hole 282 is shown for ease of illustration), which may be radiation from a patient injected with a radiopharmaceutical. The radiation is collimated and illumination results on the other side of the collimator holes, which is detected by a single pixel 284. As can be seen, in various embodiments, the collimator holes 282 of the registered collimator provide for collimation of received radiation such that the radiation (e.g., radiation energy) impinges on a single pixel 284 in the active or live area (e.g., detection area) of that pixel 284 and not within a dead area 286 (e.g., dead edges) between the pixels 284. Accordingly, increased or maximum resolution and sensitivity are provided compared to a non-registered arrangement 290. Thus, various embodiments provide a registered collimator 280 having holes 282 that are matched or aligned to the individual crystal pixels 284 of the CZT detector in both shape and location.

Accordingly, various embodiments can increase the sensitivity of an MBI camera. The increased sensitivity can be used, for example, for improved workflow and productivity or for reduced dose and increased patient population.

It should be noted that various embodiments of CZT detectors may be used in different specific applications that use the properties of these detectors including, for example, high spatial resolution, low dead space, and/or higher energy resolution.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, solid state disk drive (e.g., flash RAM), and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

As used herein the term "computer readable medium" may include a tangible and non-transitory medium. The above examples are exemplary only, and are thus not intended to limit in any way the definition and/or meaning of the term "computer readable medium".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A molecular breast imaging (MBI) system comprising:
   at least one cadmium zinc telluride (CZT) detector having a plurality of pixels; and
   a registered parallel hole collimator coupled to a face of the CZT detector and having a plurality of collimator holes, wherein the plurality of collimator holes are aligned with the plurality of pixels, the spatial dimensions of the plurality of holes are configured based on characteristics of the CZT detector and the registered parallel hole collimator, and the registered parallel hole collimator is configured to provide a detector spatial resolution of about 2.5 millimeters independent of received energy.

2. The MBI system of claim 1, wherein the registered parallel hole collimator comprises an optimized registered parallel hole collimator.

3. The MBI system of claim 2, wherein the optimized registered parallel hole collimator includes the plurality of collimator holes optimized for a dual-headed CZT detector.

4. The MBI system of claim 1, further comprising a pair of CZT detectors configured to immobilize a breast therebetween.

5. The MBI system of claim 1, wherein a height of the registered parallel hole collimator is about 2 centimeters and a pitch is about 2.5 millimeters, with a 9:1 aspect ratio.

6. The MBI system of claim 1, wherein the registered parallel hole collimator is configured having a height of between about 10 millimeters and about 30 millimeters, and the plurality of collimator holes are configured having a hole size of between about 1 millimeter and 3 millimeters.

7. The MBI system of claim 1, wherein each of the plurality of collimator holes is configured to collimate received radiation to impinge upon a single pixel of the plurality of pixels and not within a dead area between the plurality of pixels.

8. A molecular breast imaging (MBI) system comprising:
   at least one cadmium zinc telluride (CZT) detector having a plurality of pixels; and
   a registered parallel hole collimator coupled to a face of the CZT detector and having a plurality of collimator holes, wherein the plurality of collimator holes are aligned with the plurality of pixels, and the spatial dimensions of the plurality of holes are configured based on characteristics of the CZT detector and the registered parallel hole collimator, and the spatial dimensions of the plurality of collimator holes are configured having a collimator resolution of no greater than 5 millimeters full width at half maximum (FWHM) at a 2.5 centimeter distance from the registered parallel hole collimator.

9. A molecular breast imaging (MBI) system comprising:
   at least one cadmium zinc telluride (CZT) detector having a plurality of pixels; and
   a registered parallel hole collimator coupled to a face of the CZT detector and having a plurality of collimator holes, wherein the plurality of collimator holes are aligned with the plurality of pixels, a height of the registered collimator being about 2 centimeters and a pitch being about 2.5 millimeters, with a 9:1 aspect ratio.

10. The MBI system of claim 9, wherein the registered parallel hole collimator comprises an optimized registered parallel hole collimator.

11. The MBI system of claim 10, wherein the optimized registered parallel hole collimator includes the plurality of collimator holes optimized for a dual-headed CZT detector.

12. The MBI system of claim 9, further comprising a pair of CZT detectors configured to immobilize a breast therebetween.

13. The MBI system of claim 9, wherein the spatial dimensions of the plurality of collimator holes are configured having a collimator resolution of no greater than 5 millimeters full width at half maximum (FWHM) at a 2.5 centimeter distance from the registered parallel hole collimator.

14. The MBI system of claim 9, wherein the registered parallel hole collimator is configured to provide a detector spatial resolution of about 2.5 millimeters independent of received energy.

15. The MBI system of claim 9, wherein the registered parallel hole collimator is configured having a height of between about 10 millimeters and about 30 millimeters, and the plurality of collimator holes are configured having a hole size of between about 1 millimeter and 3 millimeters.

16. A molecular breast imaging (MBI) system comprising:
    a pair of cadmium zinc telluride (CZT) detectors each having a plurality of pixels and configured to immobilize an object therebetween; and
    a registered parallel hole collimator coupled to a face of each of the CZT detectors and having a plurality of collimator holes, wherein the plurality of collimator holes are aligned with the plurality of pixels, the spatial dimensions of the plurality of holes are configured based on characteristics of the CZT detectors and registered parallel hole collimators, and further wherein the registered parallel hole collimator is configured having a height of between about 10 millimeters and about 30 millimeters, and the plurality of collimator holes are configured having a hole size of between about 1 millimeter and about 3 millimeters.

17. The MBI system of claim 16, wherein the registered parallel hole collimators comprise optimized registered parallel hole collimators.

18. The MBI system of claim 16, wherein the object is a breast.

19. The MBI system of claim 16, wherein the spatial dimensions of the plurality of collimator holes are configured having a collimator resolution of no greater than 5 millimeters full width at half maximum (FWHM) at a 2.5 centimeter distance from the registered parallel hole collimators.

20. The MBI system of claim 16, wherein a height of the registered parallel hole collimators is about 2 centimeters and a pitch is about 2.5 millimeters, with a 9:1 aspect ratio.

21. The MBI system of claim 16, wherein the registered parallel hole collimators are configured to provide a detector spatial resolution of about 2.5 millimeters independent of received energy.

22. The MBI system of claim 16, further comprising a processing unit configured to combine imaging data received from the pair of CZT detectors and reconstruct into a composite image.

* * * * *